(12) United States Patent
Lee et al.

(10) Patent No.: US 11,839,154 B2
(45) Date of Patent: Dec. 5, 2023

(54) PHENANTHROLINE-BASED COMPOUND AND OPTOELECTRONIC DEVICE COMPRISING THE SAME

(71) Applicant: GWANGJU INSTITUTE OF SCIENCE AND TECHNOLOGY, Gwangju (KR)

(72) Inventors: Kwang Hee Lee, Gwangju (KR); Hee Joo Kim, Gwangju (KR); Young Ryun Kim, Gwangju (KR)

(73) Assignee: GWANGJU INSTITUTE OF SCIENCE AND TECHNOLOGY

( * ) Notice: Subject to any disclaimer, the term of this patent is extended or adjusted under 35 U.S.C. 154(b) by 0 days.

(21) Appl. No.: 18/080,738

(22) Filed: Dec. 13, 2022

(65) Prior Publication Data

US 2023/0255108 A1 Aug. 10, 2023

(30) Foreign Application Priority Data

Feb. 8, 2022 (KR) .......................... 10-2022-0016052

(51) Int. Cl.
*H10K 85/60* (2023.01)
*H10K 30/88* (2023.01)
(Continued)

(52) U.S. Cl.
CPC ....... *H10K 85/6572* (2023.02); *C07D 471/04* (2013.01); *H01G 9/20* (2013.01);
(Continued)

(58) Field of Classification Search
CPC .... H10K 85/6572; H10K 30/88; H10K 50/84; H10K 85/30; H10K 30/85; H10K 85/50;
(Continued)

(56) References Cited

U.S. PATENT DOCUMENTS

2016/0380139 A1* 12/2016 Eickelmann ........ H01L 31/0465
438/64
2018/0019407 A1* 1/2018 Sakaino .................. H01L 31/10

OTHER PUBLICATIONS

Qi Jiang "Surface passivation of perovskite film for efficient solar cells" Nature Photonics | 460 vol. 13 | Jul. 2019 | 460-466 (Year: 2019).*

(Continued)

*Primary Examiner* — Michael Y Sun
(74) *Attorney, Agent, or Firm* — Renaissance IP Law Group LLP

(57) ABSTRACT

The present invention relates to a novel compound for improving the photostability of an optoelectronic device, and more particularly, to a novel phenanthroline-based compound, a preparation method thereof, and an optoelectronic device including the same as a passivation layer. According to the present invention, the novel phenanthroline-based compound of Formula 1 is a novel compound in which an amine group side chain is introduced into the parent nucleus of phenanthroline, and is capable of being used in a solution process due to excellent solubility in a polar solvent, and simple introduction on an n-type semiconductor organic layer (e.g., an organic photoactive layer or an electron transport layer) as a passivation layer may bring about not only an increase in stability, but also an additional increase in efficiency such as an increase in open-circuit voltage or photocurrent.

9 Claims, 7 Drawing Sheets

(51) Int. Cl.
*H10K 50/84* (2023.01)
*H10K 85/30* (2023.01)
*C07D 471/04* (2006.01)
*H01G 9/20* (2006.01)

(52) U.S. Cl.
CPC ............ *H10K 30/88* (2023.02); *H10K 50/84* (2023.02); *H10K 85/30* (2023.02)

(58) Field of Classification Search
CPC .... H10K 30/10; C07D 471/04; C07D 221/10; H01G 9/20; Y02E 10/549
See application file for complete search history.

(56) References Cited

OTHER PUBLICATIONS

Yuwei Guo "Phenylalkylammonium passivation enables perovskite light emitting diodes with record high-radiance operational lifetime: the chain length matters" Nature Communications | (2021) 12:644 (Year: 2021).*

Van de Sande "Cyclization Reactions in the Chemical Ionization Spectra of Bifunctional Alkyl Phenyl Ethers" Organic Mass Spectrometry, vol. 14, No. 4, 1979 (Year: 1979).*

S. Piril Ertem "Alkaline Stability Evaluation of Polymerizable Hexyl-Tethered Ammonium Cations" Macromol. Rapid Commun. 2022, 43, 2100610 (Year: 2022).*

* cited by examiner

PHENANTHROLINE-BASED COMPOUND AND OPTOELECTRONIC DEVICE COMPRISING THE SAME

CLAIM FOR PRIORITY

This application claims priority to Korean Patent Application No. 2022-0016052 filed on Feb. 8, 2022 in the Korean Intellectual Property Office (KIPO), the entire contents of which are hereby incorporated by reference.

BACKGROUND

1. Technical Field

The present invention relates to a novel compound for improving the photostability of an optoelectronic device, and more particularly, to a novel phenanthroline-based compound, a method of preparing the same, and an optoelectronic device including the same as a passivation layer.

2. Related Art

Perovskite and organic solar cells are currently drawing attention as the most promising next-generation solar cell candidates because of the advantages of the manufacture of devices using a solution process, a high extinction coefficient and, easy control of a bandgap of perovskite and organic semiconductor, and the manufacture of highly efficient and flexible devices based on these physical properties.

For example, in the case of an inverted perovskite solar cell, since all of electrodes, an n-type functional layer, a p-type functional layer, and a photoactive layer formed of perovskite, which constitute the solar cell, can be implemented using a solution process and a low-temperature process, it can be manufactured on a flexible substrate as well as a general glass substrate, so it can be applied as a building-integrated solar cell.

However, despite the above-mentioned advantages, due to low photostability of photoactive materials constituting perovskite and organic solar cells, there is a problem in that the performance of the devices is degraded. For example, when perovskite is used as a photoactive layer, theoretically, it shows high power conversion efficiency, but in actual operation, an elution phenomenon of halide ions is problematic. This is caused by ionic bonding in the perovskite crystal structure. That is, in the perovskite crystal structure, halide ions are arranged in a plane, so the halide element is detached from the surface, and when the crystal structure is damaged due to the detachment, the crystals aggregate, so exciton quenching may occur.

Therefore, it is necessary to develop an optoelectronic device and a solar cell structure, which can address the instability of perovskite and an organic photoactive layer when exposed to light.

SUMMARY

To improve the disadvantages and problems of the related art as described above, the present invention is directed to providing a novel compound for improving the photostability of an optoelectronic device such as a light emitting diode or a solar cell.

The present invention is also directed to providing a method of preparing the novel compound.

The present invention is also directed to providing an optoelectronic device, which includes the novel compound as a passivation layer.

However, technical problems to be solved in the present invention are not limited to the above-described problems, and other problems which are not described herein will be fully understood by those of ordinary skill in the art from the following descriptions.

Technical Solution

One aspect of the present invention provides a novel phenanthroline-based compound represented by Formula 1 below.

[Formula 1]

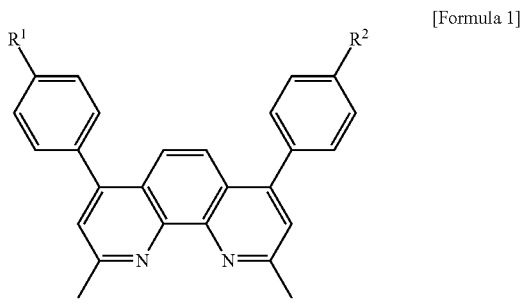

(In Formula 1,
$R^1$ and $R^2$ are each independently

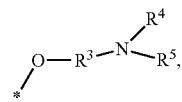

$R^3$ is $*-(CH_2)_n-*$, wherein n is an integer of 2 to 10,
$R^4$ and $R^5$ are each independently a substituted or unsubstituted $C_1$ to $C_4$ linear or branched alkyl, and
* is the binding site of a substituent.)

Specifically, n is an integer of 4 to 8, and $R^4$ and $R^5$ may each be independently substituted or unsubstituted methyl or ethyl.

More specifically, each of $R^1$ and $R^2$ may be

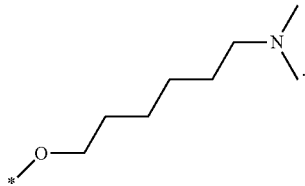 [SMILES: *OCCCCCCN(C)C]

In addition, another aspect of the present invention provides a method of preparing a novel phenanthroline-based compound. The method of preparing a novel phenanthroline-based compound includes, as shown in the following Scheme 1, preparing a compound of Formula 3 by the Suzuki reaction of a phenanthroline compound of Formula 2 having a halogen substituent in the presence of a solvent, a base and a catalyst (S10); and preparing a compound of Formula 1 by the amination of the compound of Formula 3 (S20).

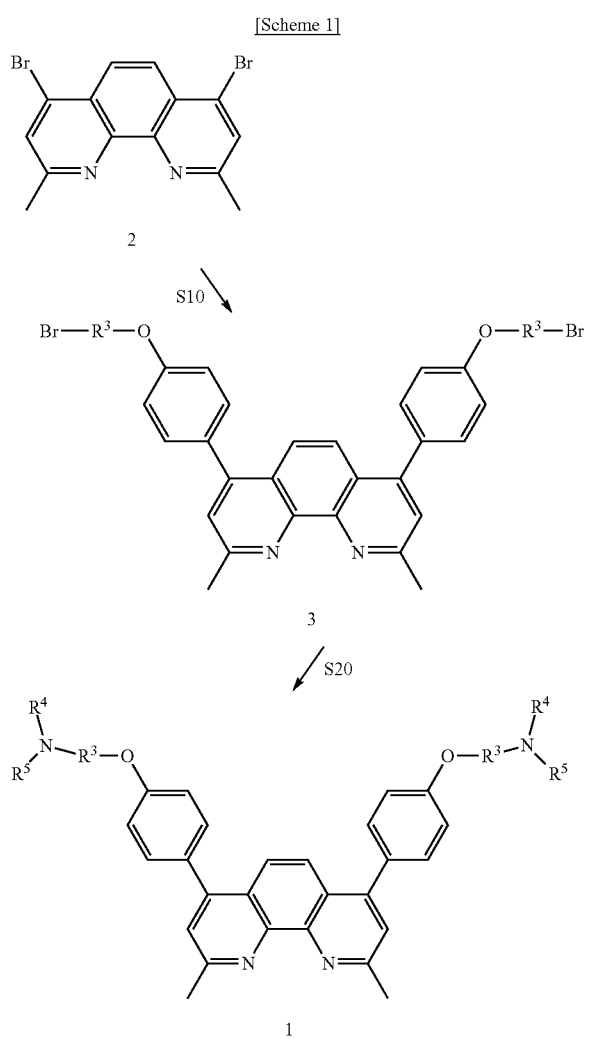

(In Scheme 1,
each of $R^3$ to $R^5$ is defined as in Formula 1 above.)

In S10, the compound of Formula 3 may be prepared by the Suzuki reaction of the phenanthroline compound of Formula 2 with a dioxoborane compound having a halogen substituent at an end.

The reaction in S10 may be performed at 80 to 120° C.

In S20, the compound of Formula 1 may be prepared by dissolving the compound of Formula 3 in an organic solvent and reacting the resultant with an amine compound.

The reaction in S20 may be performed at −100 to −50° C.

In addition, still another aspect of the present invention provides an optoelectronic device including the novel phenanthroline-based compound of Formula 1 as a passivation layer. The optoelectronic device includes a first electrode and a second electrode facing each other; a photoactive layer or light emitting layer disposed between the first electrode and the second electrode; and a passivation layer including the novel phenanthroline-based compound of Formula 1, which is disposed between the photoactive layer or light emitting layer and the second electrode.

The optoelectronic device is a perovskite solar cell, which may include a first electrode; a hole transport layer formed on the first electrode; a perovskite photoactive layer formed on the hole transport layer; an electron transport layer formed on the perovskite photoactive layer; a passivation layer including the novel phenanthroline-based compound of Formula 1 and formed on the electron transport layer; and a second electrode formed on the passivation layer.

The optoelectronic device is a perovskite light emitting diode, which may include a first electrode; a hole transport layer formed on the first electrode; a perovskite light-emitting layer formed on the hole transport layer; an electron transport layer formed on the perovskite light-emitting layer; a passivation layer including the novel phenanthroline-based compound of Formula 1 and formed on the electron transport layer; and a second electrode formed on the passivation layer.

The optoelectronic device is an organic solar cell, which may include a first electrode; a hole transport layer formed on the first electrode; an organic photoactive layer formed on the hole transport layer; a passivation layer including the novel phenanthroline-based compound of Formula 1 and formed on the organic photoactive layer; and a second electrode formed on the passivation layer.

The passivation layer may be an ultra-thin film having a thickness of 10 nm or less.

The passivation layer may inhibit defects in an n-type organic material.

In terms of the photostability of the optoelectronic device, when the perovskite solar cell was exposed to light and subjected to measurement using a maximum power point tracking method, even after 40 hours, the performance of the solar cell may be maintained at 90% of the initial efficiency.

In terms of the photostability of the optoelectronic device, when the organic solar cell is exposed to light and subjected to measurement by plotting a current-voltage curve at regular intervals, even after 40 hours, the performance of the solar cell may be maintained at 90% of the initial efficiency.

According to the present invention, a novel phenanthroline-based compound of Formula 1 is a novel compound in which an amine group side chain is introduced into the parent nucleus of phenanthroline, and it can be used in a solution process due to excellent solubility in a polar solvent, and simple introduction on an n-type semiconductor organic layer (e.g., an organic photoactive layer or an electron transport layer) as a passivation layer can bring about not only an increase in stability, but also an additional increase in efficiency such as an increase in open-circuit voltage or photocurrent.

In addition, since this compound can be used in a solution process, when a perovskite solar cell and an organic solar cell are applied to a device using a flexible substrate, a positive effect on lifespan extension can be expected, which suggests a breakthrough to improve the lifespan problem of devices with a flexible substrate. Thus, there will be an opportunity to use optoelectronic devices such as a perovskite solar cell and an organic solar cell as a next-generation energy source.

BRIEF DESCRIPTION OF DRAWINGS

Example embodiments of the present invention will become more apparent by describing in detail example embodiments of the present invention with reference to the accompanying drawings, in which.

DESCRIPTION OF EXAMPLE EMBODIMENTS

Figure 1:
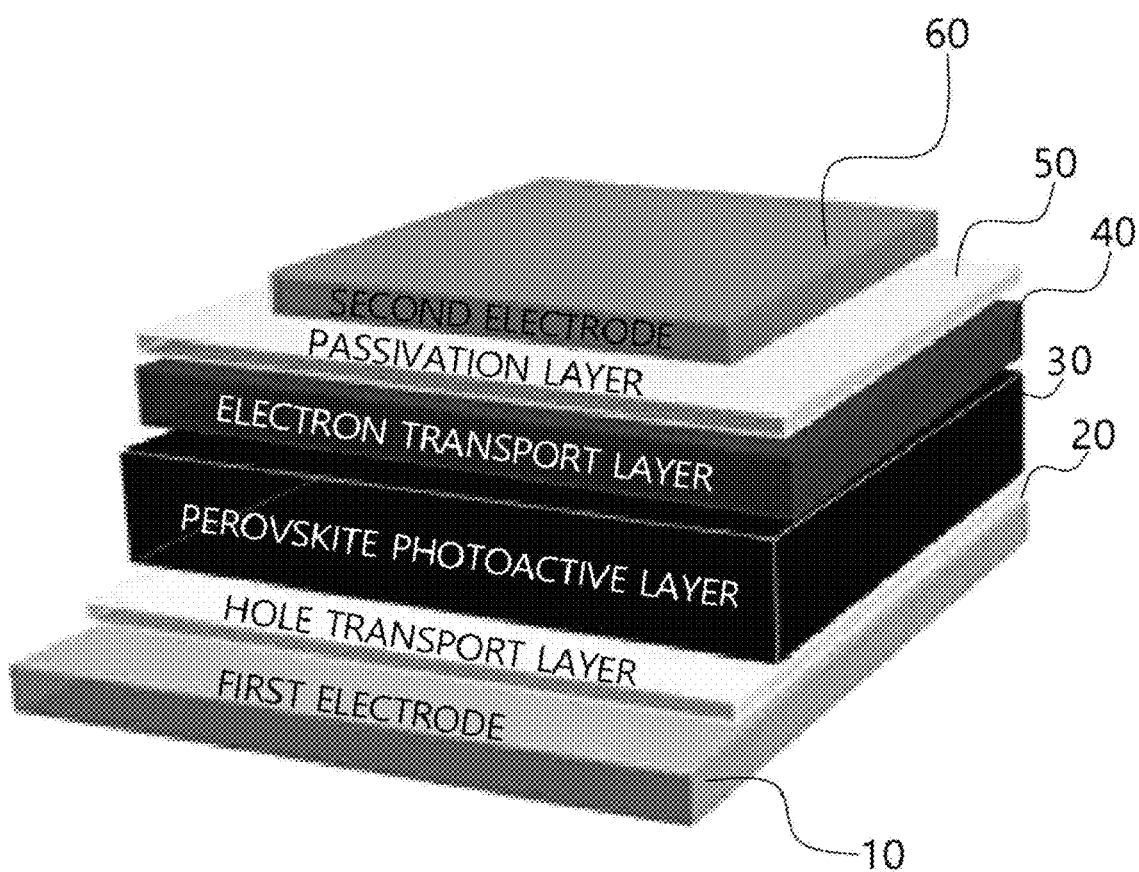
FIG. 1 is the schematic diagram of a perovskite solar cell including a passivation layer according to one embodiment of the present invention.

Since the present invention may have various modifications and various forms, specific examples are illustrated in the drawings and described in detail in the detailed description. However, it should be understood that the present invention is not limited to specific embodiments, and includes all modifications, equivalents or alternatives within the spirit and technical scope of the present invention. In description of each drawing, like numerals denote like elements.

All terms including technical and scientific terms have the same meaning that is generally understood by those skilled in the art unless defined otherwise. General terms, such as terms defined in dictionaries, should be interpreted with meanings according to the context of the related art, and should not be interpreted with ideal or excessively formal meanings unless clearly defined herein.

Hereinafter, exemplary embodiments of the present invention will be described in further detail with reference to the accompanying drawings.

Novel Phenanthroline-Based Compound

One aspect of the present invention provides a novel phenanthroline-based compound represented by Formula 1 below.

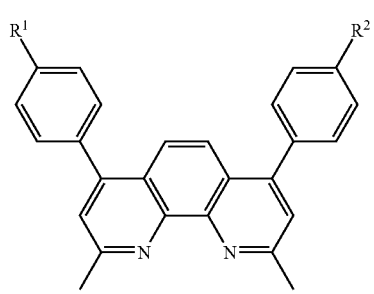

[Formula 1]

(In Formula 1, $R^1$ and $R^2$ are each independently

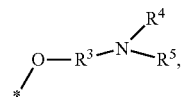

$R^3$ is $*-(CH_2)_n-*$, wherein n is an integer of 2 to 10, $R^4$ and $R^5$ are each independently substituted or unsubstituted $C_1$ to $C_4$ linear or branched alkyl, and

* is the binding site of a substituent.)

Specifically, n is an integer of 4 to 8, and $R^4$ and $R^5$ may each be independently substituted or unsubstituted methyl or ethyl.

More specifically, each of $R^1$ and $R^2$ may be

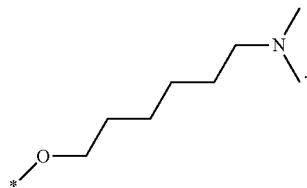 [SMILES: *OCCCCCCN(C)C]

The novel phenanthroline-based compound is a phenanthroline compound having an amine group as a side chain, and exhibits a passivation function of inhibiting the defects of an n-type semiconductor organic material generated by a light reaction in an optoelectronic device.

Method of Preparing Novel Phenanthroline-Based Compound

In addition, another aspect of the present invention provides a method of preparing a novel phenanthroline-based compound.

The method of preparing a novel phenanthroline-based compound according to the present invention includes, as shown in Scheme 1, preparing a compound of Formula 3 by the Suzuki reaction of a phenanthroline compound of Formula 2 having a halogen substituent in the presence of a solvent, a base and a catalyst (S10); and preparing a compound of Formula 1 by the amination of the compound of Formula 3 (S20).

[Scheme 1]

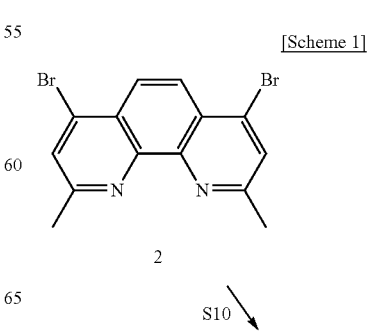

-continued

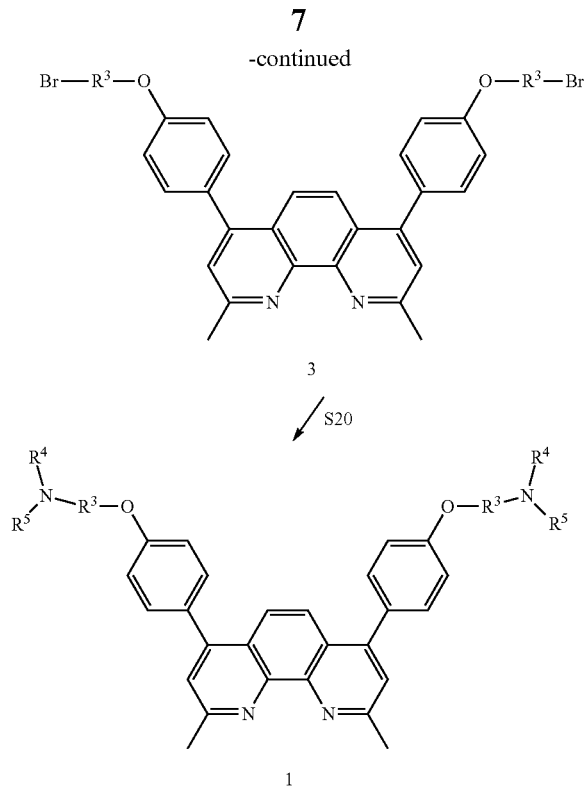

(In Scheme 1,
each of $R^3$ to $R^5$ is defined as in Formula 1 above.)

Hereinafter, the method of preparing a novel phenanthroline-based compound according to the present invention will be described in detail step by step.

First, S10 is to prepare a compound of Formula 3 by the Suzuki reaction of the phenanthroline compound of Formula 2, and specifically, to prepare a compound of Formula 3 by the Suzuki reaction of the phenanthroline compound of Formula 2 having a halogen substituent in the presence of a solvent, a base and a catalyst.

In S10, the solvent may be a mixed solvent of tetrahydrofuran and water, but the present invention is not limited thereto.

In S10, the catalyst may be tetrakis(triphenylphosphine) palladium.

In S10, for the Suzuki reaction, the phenanthroline compound of Formula 2 may react with a dioxoborane compound having a halogen substituent at an end.

The Suzuki reaction in S10 is preferably performed at 80 to 120° C., and when the reaction temperature is outside this range, there is a problem in the progress of the reaction, and there is a problem in that a number of side reactions occur.

In S10, after the reaction is completed, a purifications step using column chromatography may be further performed.

Next, S20 is to prepare the compound of Formula 1 through amination of the compound of Formula 3.

In S20, the compound of Formula 1 may be prepared by dissolving the compound of Formula 3 in an organic solvent and adding an amine compound.

In S20, the solvent may be tetrahydrofuran, but the present invention is not limited thereto.

In S20, the reaction temperature is preferably performed at −100 to −50° C., and when the reaction temperature is below a freezing temperature of a reactant, there is a problem in the progress of the reaction, and when it exceeds room temperature, there is a problem in that a number of side reactions occur.

The prepared compound of Formula 1 may further include performing high-purity purification using column chromatography.

Optoelectronic Device Including Novel Phenanthroline-Based Compound as Passivation Layer Moreover, still another aspect of the present invention provides an optoelectronic device including a novel phenanthroline-based compound as a passivation layer.

The optoelectronic device may include a perovskite-based optoelectronic device using perovskite as a photoactive layer or light emitting layer, and an organic solar cell using an organic photoactive layer, but the present invention is not limited thereto.

In one example, the optoelectronic device according to the present invention may be a perovskite solar cell, a perovskite light emitting diode, or an organic solar cell.

FIG. 1 is a schematic diagram of a perovskite solar cell according to one embodiment of the present invention.

Referring to FIG. 1, the perovskite solar cell may include a first electrode 10 and a second electrode 60, a perovskite photoactive layer 30 disposed between the two electrodes, a hole transport layer 20 disposed between the first electrode and the perovskite photoactive layer, an electron transport layer 40 disposed between the perovskite photoactive layer and the second electrode, and a passivation layer 50 including a novel phenanthroline-based compound of Formula 1 according to the present invention between the electron transport layer and the second electrode.

Figure 2:
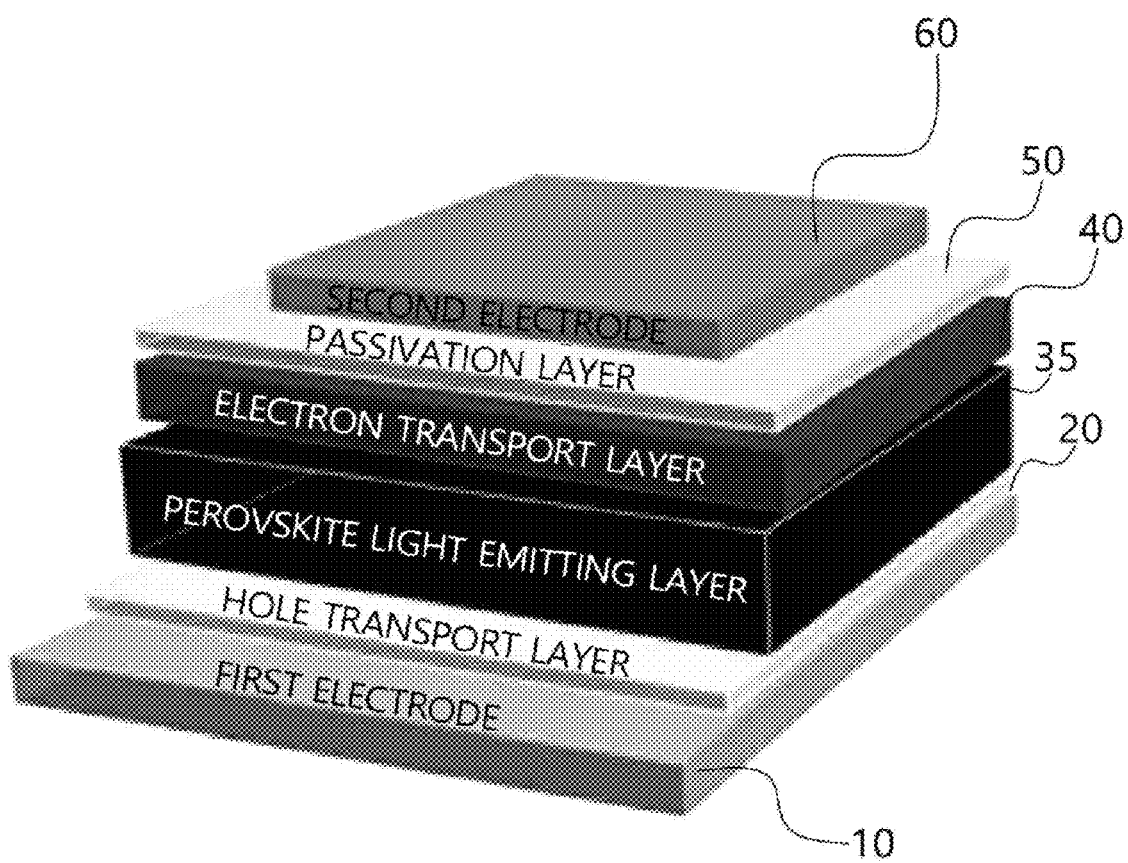
FIG. 2 is the schematic diagram of a perovskite light emitting diode including a passivation layer according to another embodiment of the present invention.

FIG. 2 is a schematic diagram of a perovskite light emitting diode according to another embodiment of the present invention.

Referring to FIG. 2, the perovskite light emitting diode may include a first electrode 10, a second electrode 60, a perovskite light emitting layer 35 disposed between the two electrodes, a hole transport layer 20 disposed between the first electrode and the perovskite light emitting layer, an electron transport layer 40 disposed between the perovskite light emitting layer and the second electrode, and a passivation layer 50 including the novel phenanthroline-based compound of Formula 1 according to the present invention between the electron transport layer and the second electrode.

Figure 3:
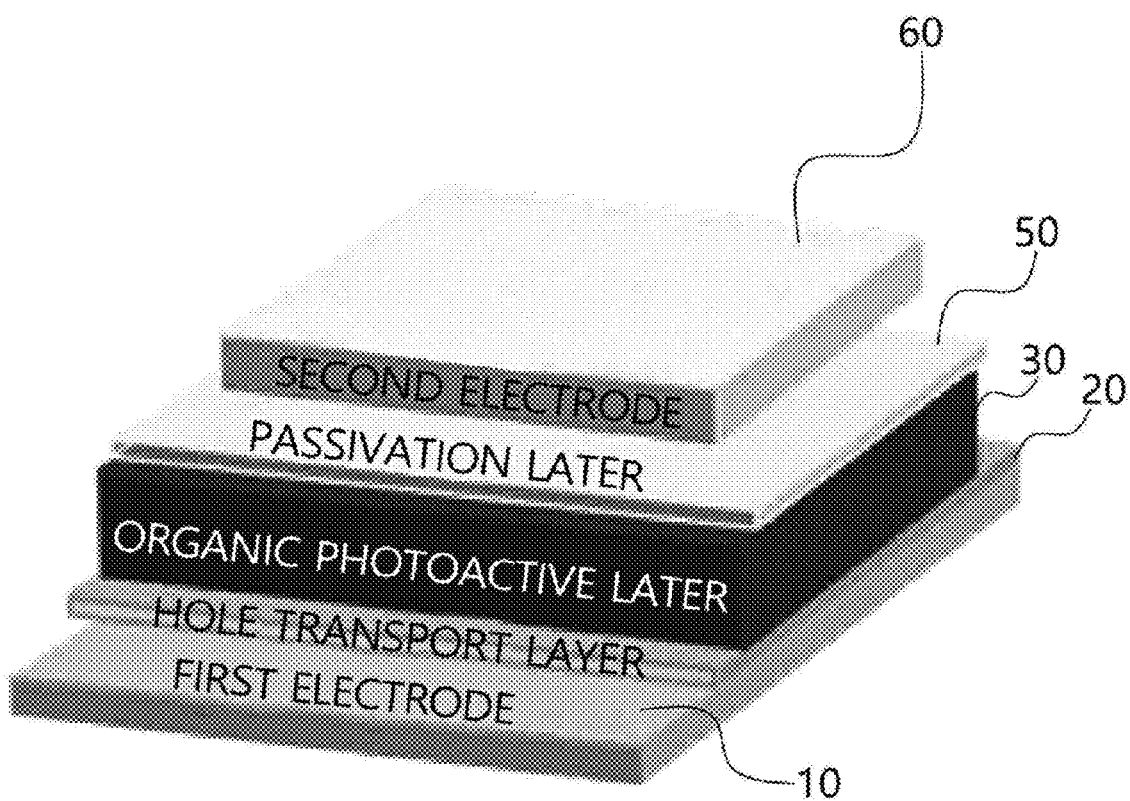
FIG. 3 is the schematic diagram of an organic solar cell including a passivation layer according to still another embodiment of the present invention.

FIG. 3 is a schematic diagram of an organic solar cell according to still another embodiment of the present invention.

Referring to FIG. 3, the organic solar cell may further include a first electrode 10, a second electrode 60, an organic photoactive layer 30 disposed between the two electrodes, a hole transport layer 20 disposed between the first electrode and the organic photoactive layer, and a passivation layer 50 including the novel phenanthroline-based compound of Formula 1 according to the present invention disposed between the organic photoactive layer and the second electrode.

The novel phenanthroline-based compound of Formula 1 may have an amine group at an end to have a passivation function, and prevent defects of an n-type semiconductor organic material. Accordingly, as the thin film of the novel phenanthroline-based compound of Formula 1, as a passivation layer, was introduced on the electron transport layer or organic photoactive layer including an n-type semiconductor organic material, defects of a perovskite-based or organic solar cell or a light emitting diode are inhibited without modification of the photoactive layer or light emitting layer, and thus it was confirmed that an enhanced photostability can be ensured even when an optoelectronic device was exposed to light and electrochemical performance can be improved (see FIGS. 4 to 6).

Therefore, the thin film of the novel phenanthroline-based compound of Formula 1 having an amine group at an end may be effectively used as a passivation layer by resolving charge imbalance in an optoelectronic device such as a perovskite device, which includes an n-type semiconductor organic material layer, or an organic solar cell.

The passivation layer may be formed of an ultra-thin film of 10 nm or less.

The passivation layer may be applied by spin coating, bar coating, spray coating, slot-die coating, gravure coating, blade coating, screen printing, nozzle printing, inkjet printing, electrohydrodynamic jet printing, electrospray or electrospinning.

Such an optoelectronic device may have the improved photostability compared to the related art.

The first electrode 10 may be, as a bottom electrode, a conductive metal oxide, a metal, a metal alloy, or a carbon material. The conductive metal oxide may be indium tin oxide (ITO), fluorine tin oxide (FTO), antimony tin oxide (ATO), fluorine-doped tin oxide (FTO), $SnO_2$, ZnO, or a combination thereof. As the anode 10, suitable metals or metal alloys may be Au and CuI. The carbon material may be graphite, graphene, or carbon nanotubes. The first electrode may be formed on the substrate. The substrate may be a glass substrate, or may be in the form of a sheet made of a flexible material. In one example, the first electrode may be an ITO electrode formed on the glass substrate.

The hole transport layer 20 may be formed on the first electrode. In one example, the hole transport layer may include, as a p-type semiconductor, poly(3,4-ethylenedioxythiophene):polystyrene sulfonate (PEDOT:PSS). In addition, the hole transport layer may use a hole transport material conventionally used in the art.

General hole transport materials may include, for example, N,N-dicarbazolyl-3,5-benzene (mCP); poly(3,4-ethylenedioxythiophene):polystyrenesulfonate (PEDOT:PSS); N,N'-di(1-naphthyl)-N,N'-diphenylbenzidine (NPD); N,N'-diphenyl-N,N'-di(3-methylphenyl)-4,4'-diaminophenyl (TPD); N,N'-diphenyl-N,N'-dinaphthyl-4,4'-diaminobiphenyl; N,N,N'N'-tetra-p-tolyl-4,4'-diaminobiphenyl; N,N,N'N'-tetraphenyl-4,4'-diaminobiphenyl; a porphyrin compound derivative such as copper(II)1,10,15,20-tetraphenyl-21H,23H-porphyrin; 1,1-bis[4-[N,N'-di(p-tolyl)amino]phenyl]cyclohexane (TAPC); a triarylamine derivative such as N,N,N-tri(p-tolyl)amine or 4,4',4'-tris[N-(3-methylphenyl)-N-phenylamino]triphenylamine; a carbazole derivative such as N-phenylcarbazole and polyvinylcarbazole; a phthalocyanine derivative such as metal-free phthalocyanine or copper phthalocyanine; a starburst amine derivative; an enamine stilbene-based derivative; a derivative of an aromatic tertiary amine and a styryl amine compound; and a polysilane.

The photoactive layer 30 or light emitting layer 35 may be formed on the hole transport layer 20. The photoactive layer or light emitting layer may include a perovskite material or an organic material.

Here, the perovskite material may be suitably selected depending on the type of device. That is, a perovskite material may be selected depending on a solar cell or light emitting diode as needed. As the perovskite material, one that is known in the art may be used, and for example, formamidinium lead bromide ($FAPbBr_3$), formamidinium lead bromine chloride ($FAPbBr_2Cl$), or methylammonium lead iodide ($MAPbI_3$) may be used, but the present invention is not limited thereto.

Here, as an organic material constituting the organic photoactive layer used in an organic solar cell, a material known in the art, for example, a material having a heterojunction of a p-type semiconductor organic material and an n-type semiconductor organic material may be used.

The electron transport layer 40 may be formed on the perovskite photoactive layer or light emitting layer. The electron transport layer may serve to increase electron injection or transport efficiency from the second electrode to the perovskite thin film.

In the electron transport layer 40, as an n-type semiconductor, a C60 derivative [6,6]-phenyl-C61-butyric acid methyl ester (PCBM) may be included, and the n-type semiconductor may be diphenylphosphine oxide-4-(triphenylsilyl)phenyl (TSPO1), 1,3,5-tris(N-phenylbenzimidazol-2-yl)benzene (TPBi), tris(8-quinolinolate)aluminum (Alq3), 2,5-diaryl silol derivative (PyPySPyPy), a perfluorinated compound (PF-6P), octasubstituted cyclooctatetraene (COT), TAZ (see the following Formula), 4,7-diphenyl-1,10-phenanthroline (Bphen), BCP (see the following Formula), or BAlq (see the following Formula).

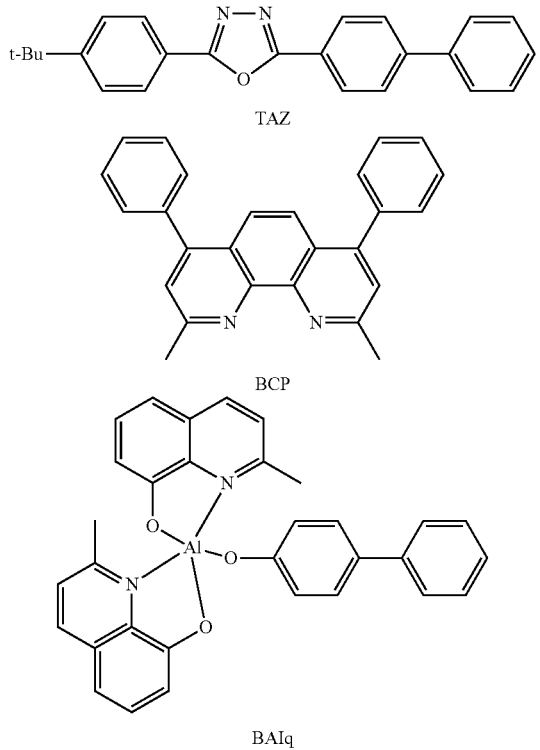

The second electrode 60 may be formed on the passivation layer 50.

The second electrode 60 may be a cathode into which an electron is injected, and may consist of a conductive material. When the second electrode 60 is a cathode, it is preferably a metal, and it may be formed using, for example, a metal such as aluminum, magnesium, calcium, sodium, potassium, indium, yttrium, lithium, silver, lead or cesium, or a combination of two or more thereof.

Meanwhile, according to one embodiment of the present invention, the first electrode 10 may be used as a cathode, and the second electrode 60 may be used as a anode. That is, a structure in which the second electrode 60 is formed on the substrate, the passivation layer 50, the electron transport layer 40, the photoactive layer 30 or the light emitting layer 35, the hole transport layer 20, and the first electrode 10 are stacked on the second electrode 60 is also included in the scope of the present invention.

The first electrode 10 or the second electrode 60 may be formed using physical vapor deposition (PVD), chemical vapor deposition (CVD), sputtering, pulse laser deposition (PLD), evaporation, electron beam evaporation, atomic layer deposition (ALD), and molecular beam epitaxy deposition (MBE).

Hereinafter, a method of manufacturing an optoelectronic device including a passivation layer according to one embodiment of the present invention will be described with reference to the structure of FIG. 1.

First, a substrate may be prepared, and a first electrode 10 may be formed on the substrate. Such a first electrode may be formed using deposition or sputtering.

Subsequently, a hole transport layer 20 may be formed on the first electrode 10. Such a hole transport layer may be formed by performing spin coating, dip coating, thermal deposition or spray deposition.

Subsequently, a photoactive layer 30 may be formed on the hole transport layer 20. The photoactive layer may be, for example, a perovskite thin film. A perovskite material may have excellent optoelectronic properties (e.g., high extinction coefficient, small exciton binding energy, long exciton diffusion length and optical gap tunability). The perovskite material of the embodiment may be an organic-inorganic perovskite (OIP) material and may have a composition or structure for enhancing power conversion efficiency. As described above, the perovskite material may be suitably selected according to the type of device, but the present invention is not limited thereto. For example, the perovskite material may have the structure of $ABX_3$, $A_2BX_4$, $A_3BX_5$, $A_4BX_6$, $ABX_4$ or $A_{n-1}Pb_nX_{3n+1}$ (n is an integer of 2 to 6), wherein A may include an organic ammonium ion, an organic amidinium ion, an organic phosphonium ion, an alkali metal ion or a derivative thereof, B may include a transition metal, rare earth metal, an alkaline earth metal, an organic material, an inorganic material, ammonium, a derivative thereof, or a combination thereof, and X may include an halogen ion or a combination of different halogen ions.

The perovskite thin film may be a bulk polycrystalline thin film or a thin film consisting of nanocrystal particles, and the nanocrystal particles may have a structure having a core-shell structure or a gradient composition.

The perovskite thin film may be formed using bar-coating, spray coating, slot-die coating, gravure coating, blade-coating, screen printing, nozzle printing, inkjet printing, electrohydrodynamic-jet printing, electrospray, or electrospinning.

Subsequently, an electron transport layer 40 may be formed on the photoactive layer 30. The electron transport layer may include [6,6]-phenyl-C61-butyric acid methyl ester (PCBM) as an n-type semiconductor. The electron transport layer may be formed by spin-coating, dip coating, thermal deposition, or spray deposition.

Next, a passivation layer 50 may be formed on the electron transport layer 40. The passivation layer preferably includes a compound of Formula 1.

The thickness of the passivation layer 50 is preferably 1 to 10 nm, and when the thickness of the passivation layer is more than 10 nm, there is a problem in that charge injection is decreased due to an insulating property.

The passivation layer 50 may be formed using spin coating, bar coating, spray coating, slot-die coating, gravure coating, blade coating, screen printing, nozzle printing, inkjet printing, electrohydrodynamic jet printing, electrospray or electrospinning.

A second electrode 60 may be formed on the passivation layer 50. The second electrode 60 may be formed using deposition or sputtering.

Hereinafter, to help in understanding the present invention, preparation examples and experimental examples will be suggested. However, the following preparation examples and experimental examples are merely provided to more easily understand the present invention and not to limit the present invention.

Preparation Example 1

Preparation of 6,6'-{(2,9-dimethyl-1,10-phenathrolin-4,7-diyl)bis[(4,1-phenylene)oxy]}bis(N,N-dimethylhexan-1-amine) (1a)

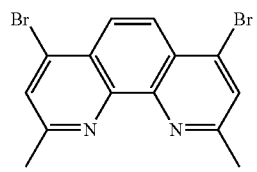

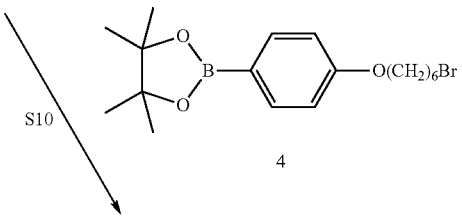

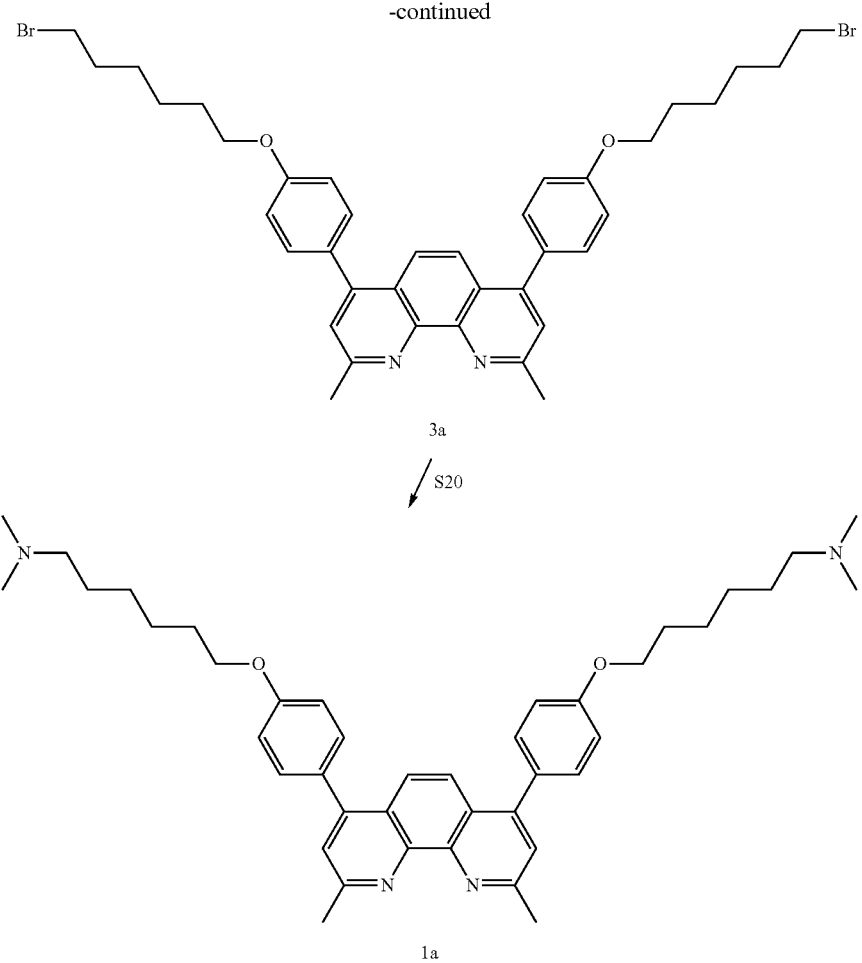

(1) Preparation of 4,7-bis[4-((6-bromohexyl)oxy)phenyl] 2,9-dimethyl-1,10-phenanthroline (3a) (S10)

4,7-dibromo-2,9-dimethyl-1,10-phenanthroline (2) (4.00 g, 10.9 mmol), 2-[4-[(6-bromohexyl)oxy]phenyl]-4,4,5,5-tetramethyl-1,3,2-dioxoborane (4) (9.60 g, 25.1 mmol), and potassium carbonate (4.52 g, 32.7 mmol) were dissolved in a mixed solution of tetrahydrofuran (120 ml) and water (30 ml), and as a catalyst, tetrakis(triphenylphosphine)palladium (3 mol %) was added and reacted at room temperature. The resultant was refluxed at 100° C. until the reaction was completed and then cooled to room temperature, and water and methylene chloride were added. The reaction mixture was washed three times with 100 ml water and distilled under vacuum to obtain a yellow oil, which was purified through column chromatography, thereby obtaining a compound (3a) (7 g, 89%) as a yellow oil.

1H NMR (300 MHz, CDCl$_3$): δ (ppm) 7.807 (s, 2H) 7.512 (s, 2H) 7.444 (d, 4H, J=8.2 Hz) 7.033 (d, 4H, J=8.2 Hz) 4.045 (t, 4H, J=6.4 Hz) 3.438 (t, 4H, J=6.5 Hz) 2.989 (s, 6H) 2.00-1.78 (m, 8H) 1.60-1.50 (m, 8H);

13C NMR (75 MHz, CDCl3): δ (ppm) 159.324, 158.558, 148.602, 145.385, 130.940, 130.189, 124.843, 124.077, 122.974, 114.549, 67.859, 33.868, 32.658, 29.073, 27.924, 25.719, 25.320.

HRMS (m/z, FAB+) for $C_{38}H_{43}Br_2N_2O_2$: calculated value—717.1694, measured value—717.1691.

(2) Preparation of 6,6'-{(2,9-dimethyl-1,10-phenanthroline-4,7-diyl)bis[(4,1-phenylene)oxy]}bis(N,N-dimethyl-hexan-1-amine) (1a) (S20)

The compound (3a) obtained in (1) (4.5 g, 6.26 mmol) was dissolved in 80 ml of tetrahydrofuran, and stirred at −78° C. for 30 minutes. Afterward, dimethylamine (62.6 ml, 125.3 mmol) was added and stirred at room temperature until the end of the reaction. Subsequently, 0.1 M sodium hydroxide was added to terminate the reaction, and ethyl acetate and water were added. The reaction mixture was washed three times with 100 ml of water and distilled under vacuum to obtain a yellow oil, which was purified through column chromatography, thereby obtaining a compound (1a) (2.5 g, 62%) as a light yellow solid.

1H NMR (300 MHz, CDCl3): δ (ppm) 7.797 (s, 2H) 7.455 (d, 4H, J=8.9 Hz) 7.422 (s, 2H) 7.040 (d, 4H, J=8.8 Hz) 4.050 (t, 4H, J=6.5 Hz) 2.979 (s, 6H) 2.312 (t, 4H, J=7.0 Hz) 2.249 (s, 12H) 1.92-1.80 (m, 4H) 1.60-1.48 (m, 8H), 1.48-1.38 (m, 4H);

13C NMR (75 MHz, CDCl3): δ (ppm) 159.263, 158.543, 148.249, 146.028, 130.909, 130.342, 124.782, 123.878, 122.882, 114.503, 68.028, 59.771, 45.464, 29.226, 27.649, 27.266, 26.071, 25.902.

HRMS for $C_{42}H_{54}N_4O_2$ (m/z, EI+): calculated value—646.4250, measured value—646.4247.

Example 1

Manufacture of Inverted Perovskite Solar Cell Including Compound of Formula 1 According to the Present Invention as Passivation Layer An inverted perovskite solar cell having the same structure as shown in FIG. 1 was manufactured.

Specifically, as a first electrode 10, a substrate (ITO/glass substrate) including an ITO-containing electrode was washed sequentially with deionized water, acetone, and isopropyl alcohol (IPA) for 20 minutes each in an ultrasonic cleaner.

Next, after the washed ITO was surface-treated using an UV-ozone cleaner for 30 minutes, to form a hole transport layer 20, a solution in which poly[bis(4-phenyl)(2,5,6-trimethylphenyeamine] (PTAA) was diluted in a toluene (Aldrich) solvent to 0.25 mg/ml was used to coat a ITO/glass substrate with PTAA through spin coating at 5000 rpm for 30 seconds, and (poly[9,9-bis(3'-(N,N-dimethyl)-N-ethyl-ammonium-propyl-2,7-fluorene)-alt-2,7-(9,9-dioctylfluorene)]dibromide) (PFN-Br) was diluted in methanol (Aldrich) to 0.5 mg/ml and used in a solution state to coat the resulting substrate at 5000 rpm for 30 seconds, thereby forming a PFN-Br/PTAA thin film.

Subsequently, to form a perovskite photoactive layer 30, a solution in which $PbI_2$ and MAI (1.5 mol) were dissolved in dimethylformamide (DMF)/(dimethyl sulfoxide (DMSO) (8:1) was applied to the PFN-Br/PTAA thin film-coated substrate and spin-coated at 5000 rpm for 30 seconds to form a perovskite thin film. To form a crystallinity of the perovskite thin film, during the spin coating with the perovskite solution, a diethyl ether (DEE) solution was dropped after 5 seconds of the start of spin coating. After spin coating, the perovskite thin film-formed substrate was dried on a hot plate maintained at 100° C. for 10 minutes.

Subsequently, to form an electron transport layer 40, a solution in which phenyl-C61-butyric-acid-methyl-ester (PCBM) was dissolved in chlorobenzene (Aldrich) at 20 mg/ml was used to coat the perovskite layer using spin coating at 2000 rpm for 30 seconds.

Afterward, a solution in which the compound of Formula 1a synthesized in Preparation Example 1 was diluted in methanol to 0.05 wt % was used to coat the electron transport layer using spin coating at 5000 rpm for 30 seconds, thereby forming a passivation layer 50.

Finally, to form an upper electrode 60, a metal electrode (copper) was formed to a thickness of 100 nm using vacuum deposition.

Example 2

Manufacture of Perovskite Light Emitting Diode Including Compound of Formula 1 According to the Present Invention as Passivation Layer A perovskite light emitting diode having a structure shown in FIG. 2 was manufactured.

First, specifically, as a first electrode 10, a substrate (ITO/glass substrate) including an electrode containing ITO was washed sequentially with deionized water, acetone and isopropyl alcohol (IPA) for 20 minutes each in an ultrasonic wave washer.

Subsequently, after the washed ITO was surface-treated using an UV-ozone cleaner for 30 minutes, to form a hole transport layer 20, a PEDOT:PSS solution was used in spin coating at approximately 3000 rpm for 30 seconds to form a thin film, and then thermally treated at 150° C. for 10 minutes.

To form a perovskite light emitting layer 35 on the hole transport layer 20, a solution in which $PbI_2$ and MAI (1.5 mol) was dissolved in dimethylformamide (DMF)/dimethyl sulfoxide (DMSO) (8:1) was applied to the substrate coated with the PEDOT:PSS thin film and spin-coated at 5000 rpm for 30 seconds to form a perovskite thin film. To form a crystallinity of the perovskite thin film, during the spin coating with the perovskite solution, a diethyl ether (DEE) solution was dropped after 5 seconds of the start of spin coating. After spin coating, the perovskite thin film-formed substrate was dried on a hot plate maintained at 100° C. for 10 minutes.

As an electron transport layer 40 formed on the light emitting layer 35, a solution in which phenyl-C61-butyric-acid-methyl-ester (PCBM) was dissolved in chlorobenzene (Aldrich) at 20 mg/ml was used to coat the perovskite layer using spin coating at 2000 rpm for 30 seconds.

Afterward, a solution in which the compound of Formula 1a synthesized in Preparation Example 1 was diluted in methanol to 0.05 wt % was used to coat the electron transport layer using spin coating at 5000 rpm for 30 seconds, thereby forming a passivation layer 50.

Finally, to form a second electrode 60, a metal electrode (copper) was formed to a thickness of 100 nm using vacuum deposition.

Example 3

Manufacture of Organic Solar Cell Including Compound of Formula 1 According to the Present Invention as Passivation Layer An organic solar cell having a structure shown in FIG. 3 was manufactured.

Specifically, as a first electrode 10, a substrate (ITO/glass substrate) including an ITO-containing electrode was washed sequentially with deionized water, acetone, and isopropyl alcohol (IPA) for 20 minutes each in an ultrasonic cleaner.

Subsequently, after the washed ITO was surface-treated using an UV-ozone cleaner for 30 minutes, to form a hole transport layer 20, a PEDOT:PSS solution was used in spin coating at approximately 3000 rpm for 30 seconds to form a thin film, and then thermally treated at 150° C. for 10 minutes.

Subsequently, a photoactive layer 30 was formed using poly[(2,6-(4,8-bis(5-(2-ethylhexyl-3-fluoro)thiophen-2-yl)-benzo[1,2-b:4,5-b']dithiophene))-alt-(5,5-(1',3'-di-2-thienyl-5',7'-bis(2-ethylhexyl)benzo[1',2'-c:4',5'-c']dithiophene-4,8-dione)] (PBDB-T-2F; PM6) as an electron-donor material, and a 2,2'-((2Z,2'Z)-((12,13-bis(2-ethylhexyl)-3,9-diundecyl-12,13-dihydro-[1,2,5]thiadiazolo[3,4-e]thieno [2",3": 4',5']thieno[2',3':4,5]pyrrolo[3,2-g]thieno[2',3':4,5]thieno[3,2-b]indole-2,10-diyl)bis(methanylylidene))bis(5,6-difluoro-3-oxo-2,3-dihydro-1H-indene-2,1-diylidene)) dimalononitrile (BTP-4F; Y6) organic material as an electron-acceptor material. That is, to form the photoactive layer, the electron-donor material PM6 and the electron-acceptor material, which is the Y6 organic material, were prepared in a glove box in a moisture-free, anaerobic atmosphere, preferably in a 1:1.2 ratio to have a concentration of 24 mg/ml and 8.8 mg/ml, respectively, and these two materials were dissolved in a chloroform solvent, 0.5% 1-chloronaphthalene solvent relative to the solution was added as an additive and then the resultant was stirred for 8 hours at 240 rpm. Afterward, the PEDOT:PSS thin film-deposited ITO substrate was moved to the glove box in a moisture-free, anaerobic atmosphere, and the PM6:Y6-mixed chloroform solution deposited on PEDOT:PSS/ITO substrate using spin coating at 3000 rpm for 30 seconds and dried in the glove box, thereby forming a photoactive layer.

Subsequently, a solution in which the compound of Formula 1a synthesized in Preparation Example 1 was diluted in methanol to 0.05 wt % was used to coat the electron transport layer using spin coating at 5000 rpm for 30 seconds, thereby forming a passivation layer 50.

Finally, to form an upper electrode 60, a metal electrode (silver (Ag)) was formed to a thickness of 100 nm using vacuum deposition.

Comparative Example 1

Manufacture of Inverted Perovskite Solar Cell Without Passivation Layer

In Example 1, an inverted perovskite solar cell was manufactured in the same manner as in Example 1, except for a process of forming a passivation layer.

Comparative Example 2

Manufacture of Perovskite Light Emitting Diode Without Passivation Layer

In Example 2, a perovskite light emitting diode was manufactured in the same manner as in Example 2, except for a process of forming a passivation layer.

Comparative Example 3

Manufacture of Organic Solar Cell Without Passivation Layer

In Example 3, an organic solar cell was manufactured in the same manner as in Example 3, except for a process of forming a passivation layer.

Comparative Example 4

Manufacture of Inverted Perovskite Solar Cell Including BCP Layer as Passivation Layer In Example 1, an inverted perovskite solar cell was manufactured in the same manner as in Example 1, except that a BCP compound of Formula a below was used instead of a compound of Formula 1a in a process of forming a passivation layer.

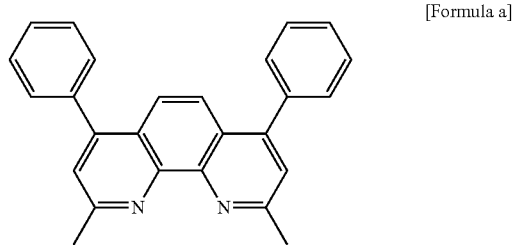 [SMILES: Cc1cc(-c2ccccc2)c2ccc3c(-c4ccccc4)cc(C)nc3c2n1]

[Formula a]

Comparative Example 5

Manufacture of Perovskite Light Emitting Diode Including BCP Layer as Passivation Layer In Example 2, a perovskite light emitting diode was manufactured in the same manner as in Example 2, except that the BCP compound of Formula a was used instead of the compound of Formula 1a in a process of forming a passivation layer.

Comparative Example 6

Manufacture of Organic Solar Cell Including BCP Layer as Passivation Layer

In Example 3, an organic solar cell was manufactured in the same manner as in Example 3, except that the BCP compound of Formula a was used instead of a compound of Formula 1a in a process of forming a passivation layer.

Experimental Example 1

Measurement of Current-Voltage Characteristic of Device According to Formation of Passivation Layer In an optoelectronic device according to the present invention, such as a perovskite solar cell or an organic solar cell, to see the change in electrochemical properties of the device according to the formation of a passivation layer consisting of a compound of Formula 1 on an organic material thin film, the following experiment was carried out.

Figure 4:
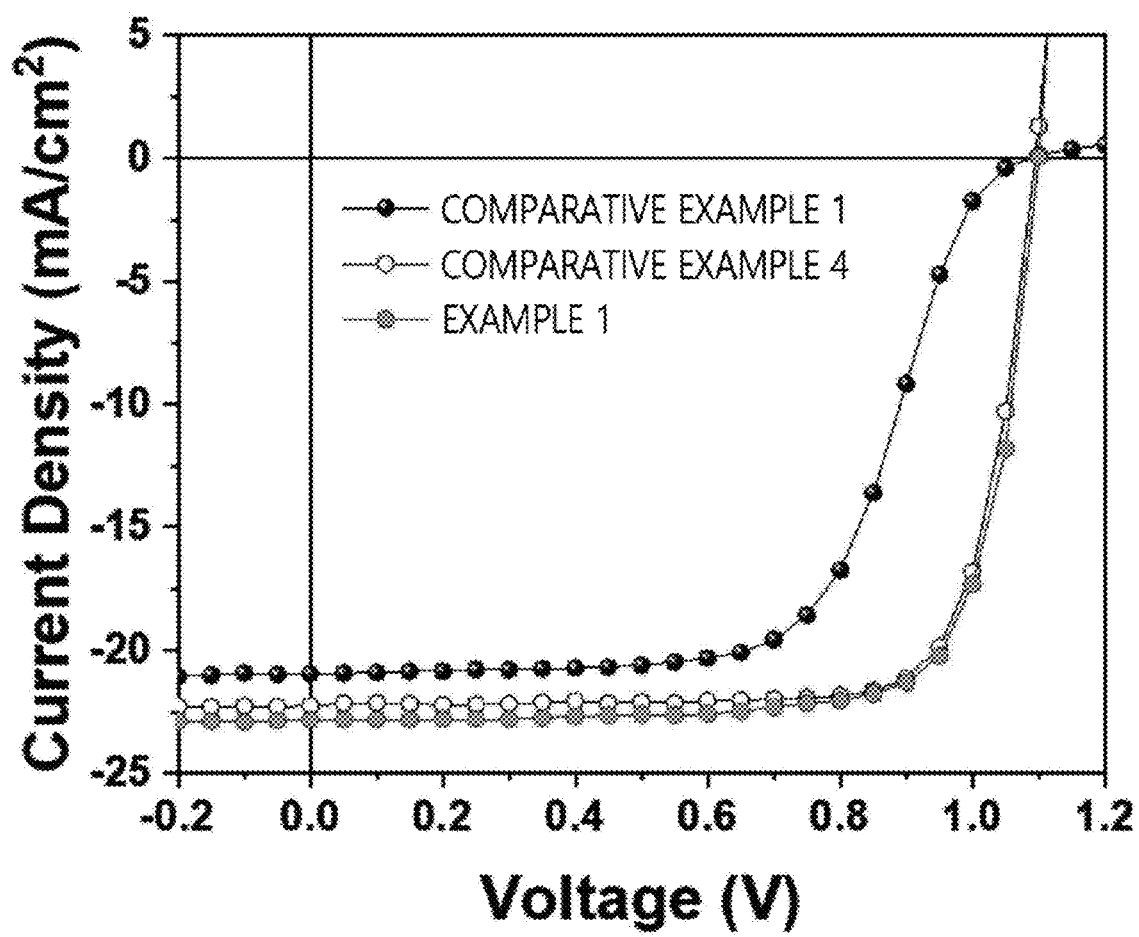
FIG. 4 shows the current-voltage curves of perovskite solar cells according to the presence or absence of a passivation layer according to an example and comparative examples of the present invention.

Specifically, in the perovskite solar cell, the current-voltage properties of the perovskite solar cell of Example 1 in which an electron transport layer was coated with the thin film of the compound of Formula 1 as a passivation layer, the perovskite solar cell of Comparative Example 4 in which an electron transport layer was coated with a BCP compound thin film, and the perovskite solar cell of Comparative Example 1 without a passivation layer were measured, and the results are shown in FIG. 4.

FIG. 4 shows the current-voltage curves of perovskite solar cells according to an example and comparative examples of the present invention.

As shown in FIG. 4, in the perovskite solar cell, when the thin film of Formula 1 was introduced as a passivation layer on an electron transport layer consisting of an n-type semiconductor organic material and when a BCP compound thin film was introduced, it can be seen that the performance of the inverted perovskite solar cell was improved.

Figure 5:
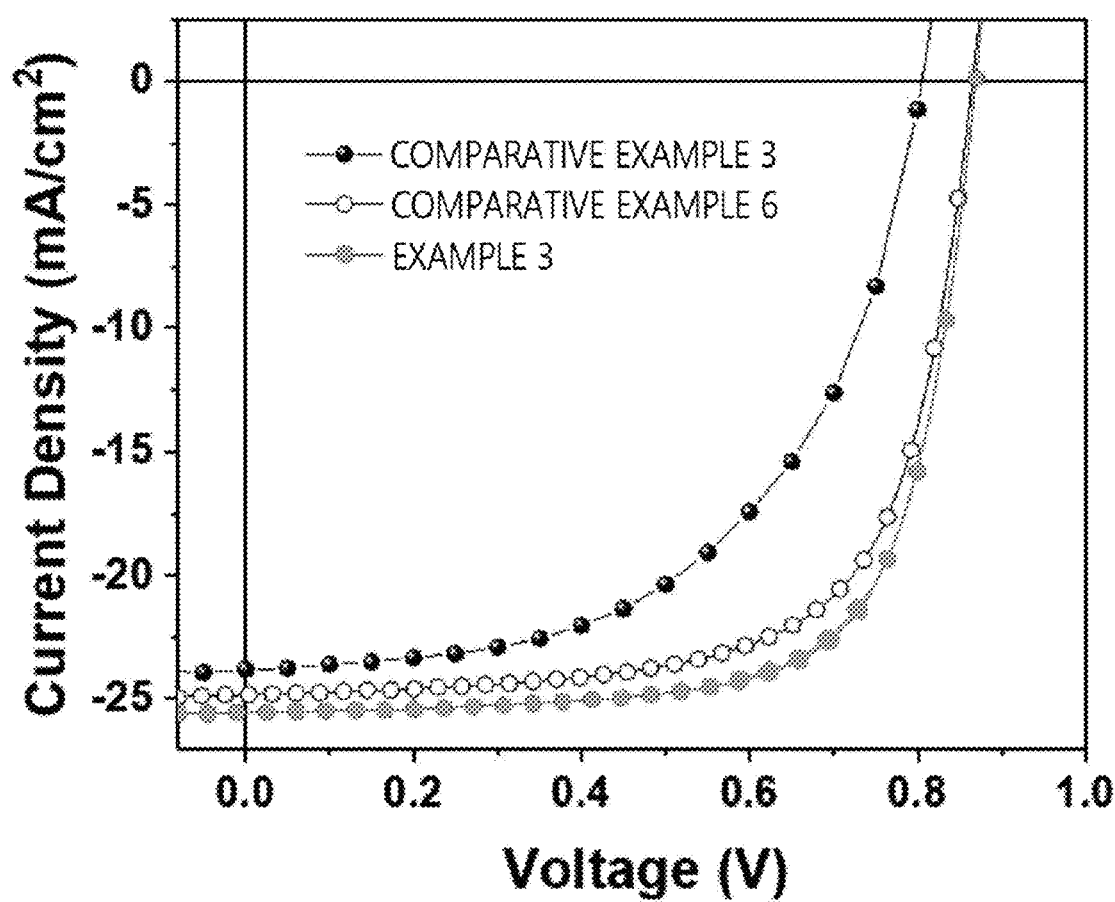
FIG. 5 shows the current-voltage curves of organic solar cells according to the presence or absence of a passivation layer according to an example and comparative examples of the present invention.

In addition, in the organic solar cell, current-voltage properties of the organic solar cell of Example 3 in which a photoactive layer including an n-type semiconductor organic material was coated with the compound thin film of Formula 1 as a passivation layer, the organic solar cell of Comparative Example 6 in which an n-type semiconductor organic material was coated with a BCP compound thin film, and the organic solar cell of Comparative Example 3 without a passivation layer were measured, and the results are shown in FIG. 5.

FIG. 5 shows the current-voltage curves of organic solar cells according to an example and comparative examples of the present invention.

As shown in FIG. 5, in the organic solar cell, when a BCP compound thin film was introduced on a photoactive layer including an n-type semiconductor organic material, the performance of the organic solar cell was improved, but when the thin film of Formula 1 was introduced as a passivation layer, it can be seen that the performance of the organic solar cell was more improved compared to the organic solar cell into which the BCP compound thin film was introduced.

Accordingly, as the phenanthroline-based compound of Formula 1 according to the present invention was introduced on the n-type semiconductor organic material as a passivation layer, the electrochemical properties of an optoelectronic device, including the perovskite solar cell and the organic solar cell, can be improved without modification of a photoactive layer.

Experimental Example 2

Measurement of Photostability of Device According to the Formation of Passivation Layer When a perovskite solar cell was exposed to light, ion defects present in the perovskite layer move upwards to destroy an electrode and an n-type functional layer. A site to which the ion defects simultaneously move induces defects in the perovskite crystal to inhibit the stability of the perovskite layer. In addition, even in the organic solar cell, the performance of the solar cell was inhibited by ion defects present in the photoactive layer due to the light exposure.

Therefore, in the optoelectronic device such as a perovskite solar cell or an organic solar cell, to see how a passivation layer consisting of the compound of Formula 1 on an organic material thin film affects the photostability of such a device, the following experiment was carried out.

Figure 6:
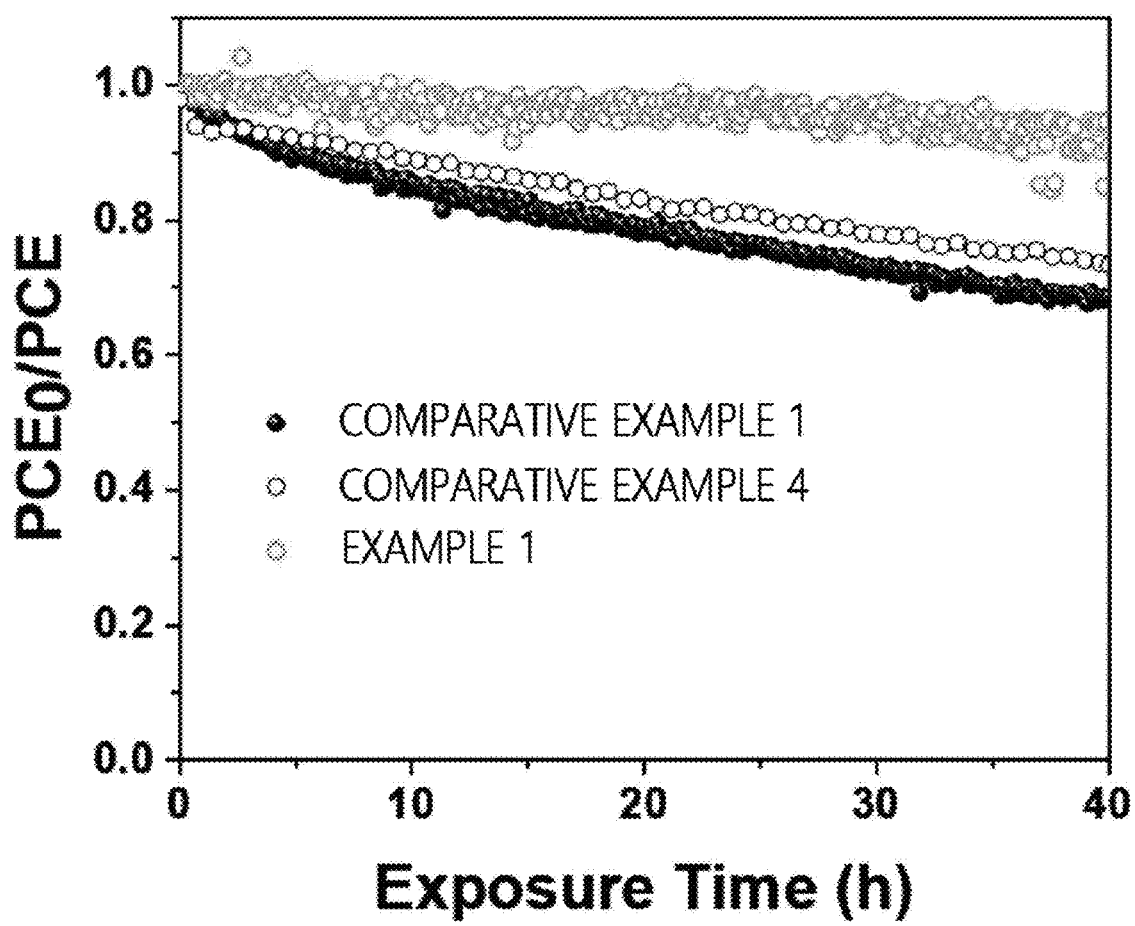
FIG. 6 is the graph showing the experimental results for the photostability of perovskite solar cells according to the presence or absence of a passivation layer according to an example and comparative examples of the present invention.

Specifically, in the perovskite solar cell, the perovskite solar cell of Example 1 in which an electron transport layer was coated with the compound thin film of Formula 1 as a passivation layer, the perovskite solar cell of Comparative Example 4 in which an electron transport layer was coated with a BCP compound thin film, and the perovskite solar cell of Comparative Example 1 without a passivation layer were exposed to solar light, and the efficiencies of the solar cells as increasing light exposure time were measured by maximum power point tracking in a nitrogen atmosphere, and the results are shown in FIG. 6.

FIG. 6 is a graph showing the experimental results for the photostability of perovskite solar cells in the presence or absence of a passivation layer according to an example and comparative examples of the present invention.

As shown in FIG. 6, in the perovskite solar cell, when the thin film of Formula 1 was introduced on an electron transport layer consisting of an n-type semiconductor organic material as a passivation layer, even after 40 hours, it was confirmed that the performance of the solar cell is maintained within 90% of the initial efficiency. However, it was shown for the perovskite solar cell of Comparative Example 4 into which the BCP compound thin film was introduced and the solar cell of Comparative Example 1 in which a passivation layer was not introduced, solar cell performance decreased to 80% of the initial efficiency within 15 and 20 hours, respectively. Therefore, in the perovskite solar cell, when the thin film of Formula 1 was introduced on the electron transport layer consisting of an n-type semiconductor organic material as a passivation layer, it was confirmed that the photostability of the inverted perovskite solar cell was also improved.

In addition, in the organic solar cell, the organic solar cell of Example 3 in which a photoactive layer including an n-type semiconductor organic material was coated with the compound thin film of Formula 1 as a passivation layer, the organic solar cell of Comparative Example 6 in which an n-type semiconductor organic material was coated with a BCP compound thin film, and the organic solar cell of Comparative Example 3 without a passivation layer were exposed to solar light, and their current-voltage curves were measured in a nitrogen atmosphere at regular intervals, thereby obtaining cell efficiency as increasing light exposure time. The results are shown in FIG. 7.

Figure 7:
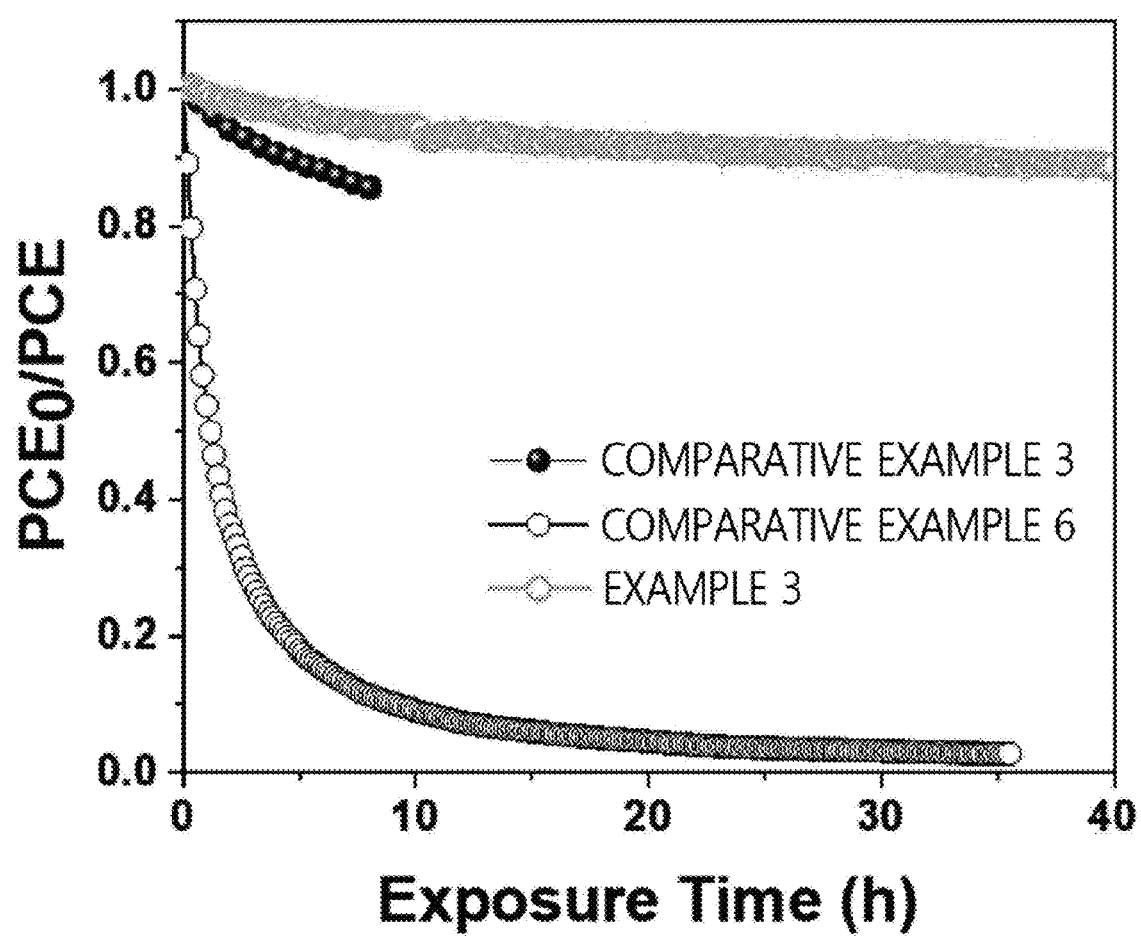
FIG. 7 is the graph showing the experimental results for the photostability of organic solar cells according to the presence or absence of a passivation layer according to an example and comparative examples of the present invention.

FIG. 7 is a graph showing the experimental results for the photostability of organic solar cells in the presence or absence of a passivation layer according to an example and comparative examples of the present invention.

As shown in FIG. 7, in the organic solar cell, when the thin film of Formula 1 was introduced on a photoactive layer including an n-type semiconductor organic material as a passivation layer, it was confirmed that the performance of the solar cell is maintained within 90% of the initial efficiency even after 40 hours. However, for the solar cell of Comparative Example 3 in which no passivation layer was introduced, solar cell performance was decreased to 80% of the initial efficiency within 10 hours. Meanwhile, in the case of the solar cell into which the BCP compound thin film was introduced, solar cell performance was decreased to 20% of the initial efficiency within 5 hours, and the cell performance stopped after 30 hours. Accordingly, in the perovskite solar cell, when the thin film of Formula 1 was introduced on an n-type semiconductor organic material as a passivation layer, it was confirmed that the photostability of the organic solar cell was also significantly improved.

Therefore, as the phenanthroline-based compound of Formula 1 according to the present invention was introduced on an n-type semiconductor organic material as a passivation layer, even when an optoelectronic device, including a perovskite solar cell and an organic solar cell, was exposed to light without modification of a photoactive layer, enhanced photostability may be ensured.

It should be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect. For example, each component described as a single unit may be distributed and implemented, and components described as being distributed may also be implemented in combined form.

The scope of the present invention is defined by the appended claims and encompasses all modifications and alterations derived from meanings, the scope and equivalents of the appended claims.

| [Description of Reference Numeral] | |
|---|---|
| 10: first electrode | 20: hole transport layer |
| 30: photoactive layer | 35: light emitting layer |
| 40: electron transport layer | 50: passivation layer |
| 60: second electrode | |

What is claimed is:
1. A novel phenanthroline-based compound represented by Formula 1 below,

[Formula 1]

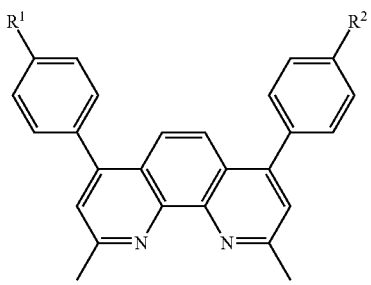

(In Formula 1,
R¹ and R² are each independently

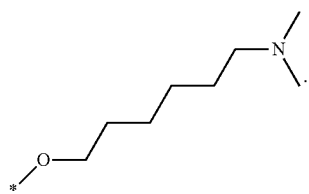

2. An optoelectronic device, comprising:
a first electrode and a second electrode facing each other;
a photoactive layer or light emitting layer disposed between the first electrode and the second electrode; and
a passivation layer comprising the novel phenanthroline-based compound of Formula 1 below and disposed between the photoactive layer or light emitting layer and the second electrode,

[Formula 1]

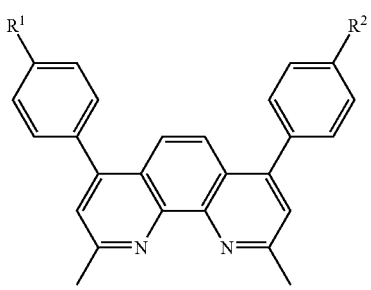

(In Formula 1,
R¹ and R² are each independently

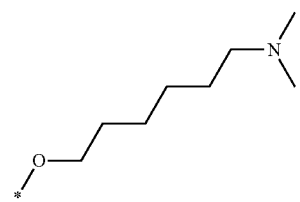

3. The device of claim 2, wherein the optoelectronic device is a perovskite solar cell, which comprises
a first electrode;
a hole transport layer formed on the first electrode;
a perovskite photoactive layer formed on the hole transport layer;
an electron transport layer formed on the perovskite photoactive layer;
a passivation layer comprising the novel phenanthroline-based compound of Formula 1 and formed on the electron transport layer; and
a second electrode formed on the passivation layer.

4. The device of claim 2, wherein the optoelectronic device is a perovskite light emitting diode, which comprises
a first electrode;
a hole transport layer formed on the first electrode;
a perovskite light-emitting layer formed on the hole transport layer;
an electron transport layer formed on the perovskite light-emitting layer;
a passivation layer comprising the novel phenanthroline-based compound of Formula 1 and formed on the electron transport layer; and
a second electrode formed on the passivation layer.

5. The device of claim 2, wherein the optoelectronic device is an organic solar cell,
a first electrode;
a hole transport layer formed on the first electrode;
an organic photoactive layer formed on the hole transport layer;
a passivation layer comprising the novel phenanthroline-based compound of Formula 1 and formed on the organic photoactive layer; and
a second electrode formed on the passivation layer.

6. The device of claim 2, wherein the passivation layer is an ultra-thin film having a thickness of 10 nm or less.

7. The device of claim 2, wherein the passivation layer inhibits defects of an n-type organic material.

8. The device of claim 3, wherein when photostability is measured through maximum power point tracking after exposing the perovskite solar cell to light, even after 40 hours, the performance of the solar cell is maintained at 90% of the initial efficiency.

9. The device of claim 5, wherein when photostability is measured by plotting a current-voltage curve at regular intervals after exposing the perovskite solar cell to light, even after 40 hours, the performance of the solar cell is maintained at 90% of the initial efficiency.

* * * * *